(12) United States Patent
Schuler et al.

(10) Patent No.: US 6,239,318 B1
(45) Date of Patent: May 29, 2001

(54) PROCESS FOR THE SELECTIVE HYDROGENATION OF HYDROFORMYLATION MIXTURES

(75) Inventors: Joachim Schuler; Alfred Kaizik; Bernhard Scholz, all of Marl; Wilfried Bueschken, Haltern; Wilhelm Droste, Marl, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/396,210

(22) Filed: Sep. 15, 1999

(30) Foreign Application Priority Data

Sep. 16, 1998 (DE) ............................................. 198 42 370

(51) Int. Cl.⁷ ...................... C07C 29/16; C07C 29/141; C07C 29/149
(52) U.S. Cl. ........................ 568/881; 568/852; 568/857; 568/882; 568/883; 568/884; 568/885; 568/909
(58) Field of Search .................................... 568/852, 857, 568/881, 882, 883, 884, 885, 909

(56) References Cited

U.S. PATENT DOCUMENTS

| | | | |
|---|---|---|---|
| 5,399,793 | 3/1995 | Vargas et al. | 568/883 |
| 5,675,045 | 10/1997 | Bueschken et al. | 568/881 |
| 5,728,891 | 3/1998 | Bueschken et al. | 568/376 |
| 5,756,856 | 5/1998 | Bueschken et al. | 568/462 |
| 5,831,135 | 11/1998 | Bueschken et al. | 568/881 |

FOREIGN PATENT DOCUMENTS

| | | |
|---|---|---|
| 1 935 900 | 2/1971 | (DE). |
| 3542595 A1 | 6/1987 | (DE). |
| 0 183 545 | 6/1986 | (EP). |
| 0 326 674 A2 | 8/1989 | (EP). |
| 0 850 905 A1 | 7/1998 | (EP). |
| 1157698 | 7/1969 | (GB). |
| 58-225033 | 12/1983 | (JP). |

OTHER PUBLICATIONS

J. Falke, New Syntheses with Carbon Monoxide, pp. 164–165; 175; 182; 184; 187; 188; 189–192; 195–195; 198; 201; 203; 210; 215; 219–220; 222–223; 225 (1981).

Kirk Othmer, Encyclopedia of Chemical Technology, vol. 17, 4$^{th}$ Edition, John Wiley & Sons, pp. 902–919 (1995).

Jv Akad. Nauk Cruz SSRSer. Khim. 16(4) 1990, pp. 287–291.

*Applied Catalysis*, 25 (1986) 181–189, Elsevier Science Publishers B.V., Amsterdam—Printed in the Netherlands.

*Primary Examiner*—Peter O'Sullivan
(74) *Attorney, Agent, or Firm*—Oblon, Spivak, McClelland, Maier & Neustadt, P.C.

(57) ABSTRACT

The invention relates to a process for the selective hydrogenation of reaction mixtures from the hydroformylation of $C_5$ to $C_{24}$ olefins using hydrogen and a supported catalyst which, as active components, comprises copper, nickel and chromium.

19 Claims, No Drawings

PROCESS FOR THE SELECTIVE HYDROGENATION OF HYDROFORMYLATION MIXTURES

BACKGROUND OF THE INVENTION

1. Field of the Invention

The invention relates to a process for the selective hydrogenation of hydroformylation mixtures which are produced in the preparation of higher oxo alcohols by hydroformylation of the corresponding olefins. The hydrogenation is selective to the extent that the aldehydes and certain byproducts of the hydroformylation are hydrogenated to give the desired alcohols, whereas the unreacted starting olefins are retained virtually completely.

2. Discussion of the Background

Higher alcohols, in particular those having from 6 to 25 carbon atoms, are known to be able to be prepared by catalytic hydroformylation (or oxo reaction) of the olefins having one carbon atom less and subsequent catalytic hydrogenation of the aldehyde- and alcohol-containing reaction mixtures. They are predominantly used as starting materials for the preparation of plasticizers or detergents.

It is known that in the catalytic hydroformylation of olefins, reaction mixtures are formed which, apart from the desired products, i.e. aldehydes and the corresponding alcohols, depending on the catalyst and the reaction conditions, can contain, in addition to unreacted olefins, by-products and secondary products of the hydroformylation, such as saturated hydrocarbons resulting from the olefins by hydrogenation, water, esters of the desired alcohols (e.g. formates), acetals of the target products aldehyde and alcohol, enol ethers and other by-products or secondary products. Said substances can be subdivided into low-boilers having a boiling point below the boiling point of the aldehyde and high-boilers having a boiling point above the boiling point of the alcohol. During the hydrogenation of the reaction mixtures, the desired alcohols are formed from some of the byproducts, such as esters and acetals, which improves the yield. On the other hand, it is desirable that the unreacted olefins remain in the hydrogenation so that they can be recirculated to the hydroformylation reaction, after separating them off from the hydrogenation mixture. Obviously, the olefins could already be separated off prior to the hydrogenation of the hydroformylation mixture by distillation of the aldehydes and the alcohols. However, this would mean an additional process step, since the hydroformylation mixture must be distilled in any case after the hydrogenation of the aldehydes.

The catalytic hydrogenation of reaction mixtures which were prepared by cobalt-catalyzed hydroformylation of olefins having from 2 to 24 carbon atoms is described in DE 35 42 595. The hydrogenation is carried out in two stages. In the first stage, the hydroformylation mixture is hydrogenated at 150–230° C. and a hydrogen pressure of 10–350 bar with 80–95% conversion on a supported $SiO_2$ catalyst which comprises 5–15% by weight of nickel and 2–20% by weight of molybdenum in the form of molybdenum oxide. In the second stage, the hydrogenation is completed at 150–230° C. and 10–350 bar hydrogen pressure on a catalyst whose active mass consists of 55–60% by weight of cobalt, 15–20% by weight of copper, 4–10% by weight of manganese and 2–5% by weight of molybdenum in the form of molybdenum oxide and, if appropriate, up to 10% by weight of activating additives. In the process, the formates and acetals present in the mixture are converted to the corresponding alcohols. The process is obviously not aimed at a selective hydrogenation with retention of the olefins, since these are not mentioned at all. Furthermore, a disadvantage in the process is that the hydrogenation is carried out in two stages and at high pressures, according to the example at 250 or 245 bar.

According to U.S. Pat. No. 5,399,793, for the hydrogenation of decobalted reaction mixtures, as arise in the hydroformylation of $C_5$–$C_{12}$ olefins, use is made of Ni/Mo catalysts on $Al_2O_3$ or $A_2lO_3SiO_2$ as support materials. The total process comprises the following individual steps:

(a) cobalt-catalyzed hydroformylation (b) decobalting of the reaction mixture (c) hydrogenation of the crude reaction mixture at elevated temperature and at elevated pressure (d) production of alcohols having very low amounts of aldehydes by distillation and (e) finish-hydrogenation of the alcohols.

The hydrogenation of stages (c) and/or (e) can be carried out using a bimetallic, phosphorus-free Ni/Mo hydrogenation catalyst. This hydrogenation catalyst produces fewer high-boiling byproducts than a corresponding phosphorus-containing catalyst. Although, in the examples, the presence of low-boilers, that is to say olefins and paraffins, is mentioned, no information is given on the mass ratio of these substances before and after the hydrogenation. It is a disadvantage in any case that to prepare an on-specification alcohol which is suitable for preparing plasticizers, two hydrogenation stages are necessary and that at least in the hydrogenation stage (b) a relatively high pressure of 1000 psig (about 70 bar) is necessary.

In addition, processes have become known in which a compound which contains a carbonyl function and an olefinic double bond is hydrogenated catalytically to the corresponding alcohol selectively retaining the olefinic double bond. Thus, according to Japanese patent application SHO 57-110354, 7-octenal is selectively hydrogenated to 7-octen-1-ol at from 70 to 150° C., use being made of a chromium oxide catalyst or a catalyst which consists of at least two of the metals chromium, copper and tin. However, this process has the disadvantage that a solvent is used which must be separated off again. In addition, the achievable space-time yields in the temperature range of from 70 to 130° C. are too low for an industrial application. At higher temperatures at which the hydrogenation rate is higher, the hydrogenation selectivity decreases rapidly owing to the unwanted hydrogenation to the saturated alcohol. At 140° C., the hydrogenation selectivity to the unsaturated alcohol is already below 95%.

In addition, citronellal may be hydrogenated to citronellol, retaining the olefinic double bond. For this purpose, according to Applied Catalysis, 25 (1986), 181–189, use is made of ruthenium catalysts and a yield of up to 90% is achieved. Using Cu/Cr catalysts, according to Iv.Akad.Nauk.Gruz SSR. Ser. Khim.16(4) (1990), 287–292, a yield of 92% was achieved.

On the other hand, it is known that 2-ethylhex-2-enal, when use is made of a Cu/Cr/Ni catalyst which contains an alkali metal component, can be hydrogenated to 2-ethylhexanol (EP 0326 674 A2). In this case, not only the carbonyl function but also the olefinic double bond are hydrogenated.

The object underlying the present invention was to hydrogenate reaction mixtures of the hydroformylation of $C_5$ to $C_{24}$ olefins under comparatively mild conditions and, in particular low pressures, selectively in such a manner that the aldehydes and certain accompanying substances present in addition to alcohols and aldehydes, in particular formates, are converted, as substantially as possible, into the desired alcohols and the unreacted olefins are hydrogenated as little as possible.

SUMMARY OF THE INVENTION

This object was surprisingly achieved by a process for the selective hydrogenation of reaction mixtures which originate from the hydroformylation of $C_5$ to $C_{24}$ olefins using hydrogen and a supported catalyst which, as active components, comprises copper, nickel and chromium.

DETAILED DESCRIPTION OF THE PREFERRED EMBODIMENTS

Preferably, use is made of the supported catalyst disclosed by EP 0 326 674 A2, which supported catalyst, as active components, comprises copper and nickel at concentrations of in each case from 0.3 to 15% by weight, chromium at a concentration of from 0.05 to 3.5% by weight and an alkali metal component at a concentration of from 0.01 to 1.6% by weight, in each case based on the supported catalyst. Another advantageous supported catalyst comprises copper, nickel and chromium in the amounts specified, but not alkali metal component. Within the context of the present invention an alkali metal is Li, Na, K, Rb and Cs.

The process according to the invention offers a number of advantages. The aldehydes in the hydroformylation mixtures are hydrogenated to the corresponding alcohols in only one hydrogenation stage at conversion rates greater than 98% at a selectivity of greater than 99%. The esters and, in particular, the formates and also the acetals are likewise converted into the desired alcohols. The starting olefins present in the mixture surprisingly remain very substantially unchanged, although the same catalysts under comparable conditions virtually quantitatively hydrogenate the olefinic double bond in 2-ethylhex-2-enal. In contrast, in the process according to the invention, less than 5% of the olefins of the starting material are hydrogenated to hydrocarbons. The hydrogenation can be carried out in the low-pressure region of below 25 bar and at high space-time yields.

The starting materials for the hydroformylation are monoolefins having from 5 to 24 carbon atoms and a terminal or middle-position C-C double bond or their mixtures, such as 1- or 2-pentene, 2-methyl-1-butane, 1-, 2- or 3-hexene, the isomeric $C_6$ olefin mixture (dipropene) produced in the dimerization of propene, 3-methyl-1-hexene, 1-octene, the isomeric $C_8$ olefin mixture (dibutene) produced in the dimerization of butenes, 1-nonene, 2-, 3- or 4-methyl-1-octane, the isomeric $C_9$ olefin mixture (tripropene) produced in the trimerization of propene, 1-, 2- or 3-decene, 2-ethyl-1-octane, 1-dodecene, the isomeric $C_{12}$ olefin mixture (tetrapropene or tributene) produced in the tetramerization of propene or the trimerization of butenes, 1-tetradecene, 1- or 2-hexadecene, $C_{16}$ olefin mixtures (tetrabutene) produced in the tetramerization of butenes, and olefin mixtures prepared by cooligomerization of olefins having different carbon numbers (preferably 2 to 4), if appropriate after separating off by distillation into fractions of identical or similar carbon number. Preferably, mixtures are hydrogenated which are produced in the hydroformylation of $C_8$, $C_9$, $C_{12}$ or $C_{16}$ olefin mixtures.

The olefins are hydroformylated in a conventional manner and then give the starting materials for the hydrogenation process according to the invention. Rhodium catalysts or preferably cobalt catalysts, are therefore employed, with or without complex-stabilizing additives, such as organic phosphines or phosphites. The temperatures and the pressures can vary, depending on catalyst and olefin, in broad ranges. A description of the hydroformylation of olefins is found, for example, in J. Falbe, New Syntheses with Carbon Monoxide, Springer-Verlag, Heidelberg-New York, 1980, pages 99ff., and in Kirk-Othmer, Encyclopedia of Chemical Technology, volume 17, 4th edition, John Wiley & Sons, pages 902–919 (1996).

The hydroformylation reaction mixtures are expediently firstly freed from the catalyst. If a cobalt catalyst was used, this can be achieved by pressure relief, separating off the aqueous catalyst phase, oxidation of the cobalt carbonyl compounds remaining in the hydroformylation mixture with air or oxygen and scrubbing out the resulting cobalt compounds with water or aqueous acid. Decobalting processes are well known, see, for example, J. Falbe, loc. cit., Kirk-Othmer, loc. cit., 164, 175, BASF process; and EP-0 850 905 A1.

If a rhodium compound served as hydroformylation catalyst, it can be separated off from the hydroformylation mixture as a distillation residue by means of thin-film evaporation.

The hydroformylation reaction mixtures expediently freed from the hydroformylation catalyst generally comprise 3–40% by weight, at most 5–30% by weight, of low-boilers, principally olefins, in addition the corresponding saturated hydrocarbons and water, 30–90% by weight of aldehydes, 5–60% by weight of alcohols, up to 10% by weight of formates of these alcohols and from 5 to 15% by weight of high-boilers. It may be emphasized, however, that the process according to the invention can also be carried out using hydroformylation mixtures whose composition does not correspond to these specifications in this or that relationship.

Preferred catalysts at which the hydroformylation mixtures are hydrogenated comprise in each case 0.3–15% by weight of copper and nickel and, as activators, 0.05–3.5% by weight of chromium and, advantageously, 0.01–1.6% by weight, preferably 0.02–1.2% by weight, of an alkali metal component on a support material, preferably aluminum oxide or silicon dioxide. The amounts specified relate to the catalyst prepared as described below, which is still not reduced. The alkali metal component can, as mentioned, alternatively be absent.

The catalyst components can be homogeneously distributed in the pores of a support material or enriched in its edge zones. In the former case, an aqueous solution is made up which comprises the components in the form of metal salts as catalyst precursor and whose volume expediently roughly corresponds to 0.8 times the pore volume of the support material. As copper salts, nickel salts or chromium salts, use is advantageously made of those which are converted on heating into oxides, such as nitrates and acetates. If the catalyst is to contain an alkali metal component, this can be introduced together with chromium in the form of alkali metal chromate or alkali metal bichromate, in particular as sodium chromate or sodium bichromate. The metal salt concentration in the solution depends on the desired concentration of the respective component in the finished catalyst. The metal salt solution is then sprayed on to the non-preheated support material, situated in a coating drum and penetrates into the pores thereof. The catalyst is then dried.

If a catalyst is desired having components which are enriched in the edge zones of a porous or a more or less pore-free support material, the metal salt solution can be sprayed onto a preheated support material and the support material can be further heated during the spraying, so that the water evaporates and the catalyst components are fixed essentially on the surface of the support material. Preparation of a supported catalyst, in which the catalyst is not homogeneously distributed on the support may be done by conventional methods known to those of ordinary skill in the art.

After the catalyst components are applied, the catalyst is calcined, i.e. depending on the catalyst precursor used, heated to temperatures of 200–400° C., which converts the catalyst precursors into the oxide state. The catalyst is then reduced with hydrogen at said hydrogenation temperatures. The reduction can be performed just after the catalyst is prepared or expediently not until the hydrogenation reactor.

The catalysts are advantageously used in a form in which they offer a low resistance to flow, e.g. in the form of granules, pellets or shaped bodies such as tablets, cylinders, rod extrudates or rings. They are expediently activated prior to use by heating in a hydrogen stream, for example at from 150 to 250° C., if they have not been reduced in the reactor.

The hydrogenation according to the invention can be carried out continuously or batchwise and either in the gas phase or in the liquid phase. Hydrogenation in the liquid phase is preferred, since the gas-phase process requires a higher energy consumption, because of the necessary circulation of large gas volumes. In addition there is the fact that evaporating aldehydes having an increasing carbon number requires more and more energy, and in addition, the starting material loading of the reduction gas decreases, so that the gas-phase process virtually can no longer be operated economically in the case of aldehydes having a carbon number greater than about 8.

Various process variants can be selected for the liquid-phase hydrogenation. It can be carried out adiabatically or virtually isothermally, i.e. having a temperature rise of <10° C., in a single stage or two stages. In the latter case, both reactors, expediently tube reactors, can be operated adiabatically or virtually isothermally or one can be operated adiabatically and the other virtually isothermally. In addition, it is possible to hydrogenate the hydroformylation mixtures in a straight pass or with product recycling. The reactors can be operated as cocurrent flow reactors with a trickle bed (trickle flow) or preferably with high liquid loadings (pulse flow). In the interest of a high space-time yield, the reactors are preferably operated with high liquid loadings of 5–100 m$^3$, in particular 15–50 m$^3$ per m$^2$ of cross section of the empty reactor and hour. If a reactor is operated isothermally and in a straight pass, the catalyst space velocity (LHSV) values can be between 0.1 and 10 h$^{-1}$, preferably between 0.5 and 5 h$^{-1}$.

The liquid-phase hydrogenation is generally carried out at an overall pressure of from 5 to 30 bar, in particular between 15 and 25 bar. The gas-phase hydrogenation can also be carried out at lower pressures, with correspondingly greater gas volumes. The reaction temperatures, in the case of hydrogenations in the liquid or gaseous phase, are generally between 120 and 220° C., in particular between 140 and 180° C.

After the hydrogenation, the reaction mixtures are worked up by distillation. This is expediently achieved at reduced pressure, e.g. at an absolute pressure of 400–900 mbar. The olefins can be recirculated to the hydroformylation.

As a result of hydrogenation, the amount of olefin in the product is preferably $\geq$90 wt. %, more preferably $\geq$93 wt. %, even more preferably $\geq$95 wt. %, even more preferably $\geq$97 wt. %, most preferably 100 wt. % of the olefin content of the starting material.

As a result of hydrogenation, the amount of aldehyde in the product is preferably $\leq$5 wt. %, more preferably $\leq$3 wt. %, even more preferably $\leq$2 wt. %, even more preferably $\leq$1 wt. % of the aldehyde content of the starting material.

The present invention is also directed to an integrated process of i) hydrogenation of a reaction mixture from hydroformylation of $C_{5-24}$ olefins; ii) separation of alcohol from olefin; and iii) hydroformylating the olefin recovered from step ii).

The present invention is also directed to an integrated process of i) hydroformylating a $C_{5-24}$ olefin; ii) hydrogenation the reaction mixture of step i); iii) separation of alcohol from olefin; and iv) recycling the olefin recovered from step ii) to step i).

Having generally described this invention, a further understanding can be obtained by reference to certain specific examples which are provided herein for purposes of illustration only and are not intended to be limiting unless otherwise specified.

EXAMPLE 1

Hydrogenation of $C_{13}$ aldehydes in the Liquid Phase

One liter of a reaction discharge, which has been freed from catalyst by thin-film evaporation, from the Rh-catalyzed hydroformylation of a $C_{12}$ olefin mixture (tributene) was hydrogenated in a recirculation apparatus at 175° C. and an overall pressure of 20 bar with hydrogen on 100 g of catalyst. The catalyst, together with aluminum oxide as support material, prior to activation with hydrogen (8 h at 200° C.) comprised 12.1% by weight of Cu 3.0% by weight of Ni and 2.5% by weight of Cr The catalyst was present in the form of rod extrudates having a bulk density of 0.67 kg/l. The analyses of starting material and product can be taken from Table 1 below.

TABLE 1

(Amounts of substance in % by weight 1/LHSV in l$_{cat}$·h/l$_{starting\ material}$)

| | 1/LHSV | Olefins | Paraffins | Aldehydes | Alcohols | Esters | High-boilers | Water |
|---|---|---|---|---|---|---|---|---|
| Starting material | 0 | 14.8 | 1.3 | 76.5 | 6.4 | 0 | 1.0 | 0 |
| Product | 1.75 | 14.3 | 1.8 | 0.5 | 82.1 | 0 | 1.3 | 0 |

It can be seen that more than 99% of the aldehydes, but only approximately 3% of the olefins were hydrogenated.

EXAMPLE 2

Hydrogenation of $C_9$ aldehydes in the Liquid Phase

One liter of a decobalted reaction discharge of the cobalt-catalyzed hydroformylation of a $C_8$ olefin mixture (dibutene) was hydrogenated with hydrogen at 170° C. in a recirculation apparatus, the overall pressure being 20 bar. 100 g of the catalyst of Example 1 was used, the liquid loading was 35 m³ per m² of reactor cross section (superficial tube) and hour.

The starting material and product analyses can be seen in Table 2 below.

TABLE 2

(Amounts of substance in % by weight, calculated as anhydrous, except for water); 1/LHSV in $l_{cat}·h/l_{starting\ material}$)

| | 1/LHSV | Olefins | Paraffins | Aldehydes | Alcohols | Esters | Methanol | High-boilers | Water |
|---|---|---|---|---|---|---|---|---|---|
| Starting material | 0 | 7.6 | 4.4 | 47.2 | 32.1 | 4.5 | 0 | 4.2 | 2 |
| Product | 0.65 | 7.3 | 4.7 | 0.3 | 82.5 | 0.1 | 0.8 | 4.3 | 2 |

It can be seen that, again, more than 99% of the aldehydes, but only approximately 4% of the olefins, were hydrogenated.

EXAMPLE 3

Hydrogenation of $C_9$ aldehydes in the Liquid Phase

One liter of a reaction discharge of the Rh-catalyzed hydroformylation of a $C_8$ olefin mixture (dibutene), which was freed from catalyst by thin-film evaporation, was hydrogenated with hydrogen at 170° C. in a recirculation apparatus, the overall pressure being 20 bar. 100 g of the catalyst of Example 1 were used, the liquid loading was again 35 m³ per m² of reactor cross section and hour.

The starting material and product analyses can be seen in Table 3 below.

TABLE 3

(Amounts of substance in % by weight; 1/LHSV in $l_{cat}·h/l_{starting\ material}$)

| | 1/LHSV | Olefins | Paraffins | Aldehydes | Alcohols | Esters | High-boilers | Water |
|---|---|---|---|---|---|---|---|---|
| Starting material | 0 | 5.4 | 0.6 | 87.9 | 4.1 | 0 | 2.0 | 0 |
| Product | 0.55 | 5.2 | 0.8 | 0.3 | 91.6 | 0 | 2.1 | 0 |

It can be seen that more than 99% of the aldehydes, but only approximately 4% of the olefins, were hydrogenated.

Obviously, numerous modifications and variations of the present invention are possible in light of the above teachings. It is therefore to be understood that within the scope of the appended claims, the invention may be practiced otherwise than as specifically described herein.

This application is based on German patent application 19842370.5 filed with the German Patent Office on Sep. 16, 1998, the entire contents of which are hereby incorporated by reference.

What is claimed is:

1. A process for the selective hydrogenation of reaction mixtures from the hydroformylation of $C_{5-24}$ olefins using hydrogen and a supported catalyst which, as active components, comprises copper, nickel and chromium.

2. The process as claimed in claim 1, wherein said supported catalyst comprises copper and nickel at concentrations of in each case from 0.3 to 15% by weight and chromium at a concentration of from 0.05 to 3.5% by weight, in each case based on the weight of the supported catalyst.

3. The process of claim 2, wherein said catalyst further comprises an alkali metal component at a concentration of from 0.01 to 1.6% by weight based on the weight of the supported catalyst.

4. The process of claim 3, wherein the concentration of said alkali metal component is 0.2–1.2% by weight.

5. The process of claim 2, wherein said supported catalyst does not comprise an alkali metal component.

6. The process of claim 1, wherein said supported catalyst is supported on a support material selected from the group consisting of silicon dioxide, aluminum oxide and a mixture thereof.

7. The process of claim 1, wherein said catalyst components are homogeneously distributed in the pores of the support material.

8. The process of claim 1, wherein said catalyst components are homogeneously enriched in the edge zones of the support material.

9. The process of claim 1, wherein said mixture is from the hydroformylation of $C_8$, $C_9$, $C_{12}$ or $C_{16}$ mixtures.

10. The process of claim 1, wherein hydrogenation is carried out continuously or batchwise in the liquid phase.

11. The process of claim 1, wherein hydrogenation is carried out in the liquid phase at an overall pressure of from 5 to 30 bar.

12. The process of claim 1, wherein the overall pressure is from 15 to 25 bar.

13. The process of claim 1, wherein hydrogenation is carried out at from 120 to 220° C.

14. The process of claim 1, wherein the temperature is from 140 to 180° C.

15. The process of claims 1, wherein hydrogenation is carried out in the liquid phase and at liquid loadings of 5–100 m$^3$ per m$^2$ of cross section of the empty reactor and hour.

16. The process of claim 1, wherein the liquid loading is 15–50 m$^3$ per m$^2$ of cross section of the empty reactor and hour.

17. The process of claim 1, further comprising separation of a hydrogenation mixture by distillation and hydroformylating said olefins.

18. A process comprising:
   i) hydrogenating a reaction mixture from the hydroformylation of C$_{5-24}$ olefins using hydrogen and a supported catalyst which, as active components, comprises copper, nickel and chromium;
   ii) separating alcohol and olefin components from said hydrogenation; and
   iii) hydroformylating said olefin from step ii).

19. A process comprising:
   i) hydroformylating C$_{5-24}$ olefins;
   ii) hydrogenating a reaction mixture from step ii) using hydrogen and a supported catalyst which, as active components, comprises copper, nickel and chromium;
   iii) separating alcohol and olefin components from said hydrogenation; and
   iv) recycling said olefin from step iii) to step i).

* * * * *